US012788229B2

(12) United States Patent
Lee et al.

(10) Patent No.: US 12,788,229 B2
(45) Date of Patent: Nov. 10, 2026

(54) ENDOSCOPE SYSTEM

(71) Applicant: MEDINTECH INC., Seoul (KR)

(72) Inventors: Chi Won Lee, Namyangju-si (KR); Myung Joon Kim, Gwacheon-si (KR)

(73) Assignee: MEDINTECH INC., Seoul (KR)

( * ) Notice: Subject to any disclaimer, the term of this patent is extended or adjusted under 35 U.S.C. 154(b) by 280 days.

(21) Appl. No.: 18/265,975

(22) PCT Filed: Sep. 27, 2021

(86) PCT No.: PCT/KR2021/013159
§ 371 (c)(1),
(2) Date: Jun. 8, 2023

(87) PCT Pub. No.: WO2023/048313
PCT Pub. Date: Mar. 30, 2023

(65) Prior Publication Data

US 2024/0090753 A1 Mar. 21, 2024

(51) Int. Cl.
*A61B 1/005* (2006.01)
*A61B 1/05* (2006.01)
*A61B 1/07* (2006.01)

(52) U.S. Cl.
CPC .............. *A61B 1/0057* (2013.01); *A61B 1/05* (2013.01); *A61B 1/07* (2013.01)

(58) Field of Classification Search
CPC ........... A61B 1/0057; A61B 1/05; A61B 1/07; A61B 1/00124; A61B 1/00126; A61B 1/0669; A61B 1/0052
See application file for complete search history.

(56) References Cited

U.S. PATENT DOCUMENTS 5,313,936 A 5/1994 Miyazaki et al.
6,236,876 B1 * 5/2001 Gruner ................. A61B 1/0016 600/407
2013/0047757 A1 * 2/2013 Okamoto ............. A61B 1/0016 74/89.22
2015/0080658 A1 3/2015 Chung et al.
2015/0313450 A1 * 11/2015 Wieth .................. A61B 1/0057 600/146
2016/0030120 A1 2/2016 Yanagihara
2018/0080533 A1 * 3/2018 Awtar .................... A61B 34/71
(Continued)

FOREIGN PATENT DOCUMENTS

CN 106455916 A 2/2017
JP 05-293076 A 11/1993
(Continued)

OTHER PUBLICATIONS

International Search Report for PCT/KR2021/013159 mailed Jun. 20, 2022 from Korean Intellectual Property Office.
(Continued)

*Primary Examiner* — Michael J Carey
*Assistant Examiner* — Christen A. Sharpless
(74) *Attorney, Agent, or Firm* — Harvest IP Law, LLP

(57) ABSTRACT

An aspect of the present invention relates to an endoscope system which can be inserted into the body of a subject to examine or treat tissue and, more specifically, to an endoscope system in which an operation of bending a bending section of an insertion tube is motorized, and thus convenience in a surgeon's manipulation is ensured.

4 Claims, 4 Drawing Sheets

(56) References Cited

U.S. PATENT DOCUMENTS

| | | | | |
|---|---|---|---|---|
| 2019/0223691 | A1* | 7/2019 | Takatsuji | A61B 1/0057 |
| 2019/0282073 | A1* | 9/2019 | Truckai | A61B 1/051 |
| 2021/0374990 | A1* | 12/2021 | Miyashita | G06T 17/00 |
| 2022/0369908 | A1* | 11/2022 | Komatsu | H02J 50/10 |

FOREIGN PATENT DOCUMENTS

| | | | | |
|---|---|---|---|---|
| JP | 05-297284 | A | 11/1993 | |
| JP | 05-329097 | A | 12/1993 | |
| JP | H05329097 | A * | 12/1993 | A61B 1/0016 |
| JP | 06-105800 | A | 4/1994 | |
| JP | 06-217926 | A | 8/1994 | |
| JP | 2002-306402 | A | 10/2002 | |
| KR | 10-2015-0030949 | A | 3/2015 | |
| WO | 2016-190273 | A1 | 12/2016 | |
| WO | 2020-243285 | A1 | 12/2020 | |
| WO | 2021-145413 | A1 | 7/2021 | |

OTHER PUBLICATIONS

Office Action of Korean Patent Application No. 10-2020-0078211 dated Oct. 17, 2021.
The extended European Search Report of European Patent Application No. 21958490.1 dated Jun. 4, 2024.
Office Action of Japanese Patent Application No. 2023-540758 dated Mar. 5, 2024.
Office Action of Japanese Patent Application No. 2023-540758 dated Jun. 18, 2024.
Office Action of Japanese Patent Application No. 2023-540758 dated Jan. 7, 2025.
Office Action From Japanese Patent Office Dated Dec. 2, 2025 Issued for Japanese Patent Application No. 2025-077473.
Chinese Search Report Dated Jun. 1, 2026 Issued for Corresponding Chinese Patent Application.
Office Action From Chinese Patent Office Dated Jun. 5, 2026 Issued for Corresponding Chinese Patent Application.
Notice of Allowance issued by CNIPA on Aug. 18, 2026.

* cited by examiner

ENDOSCOPE SYSTEM

TECHNICAL FIELD

An aspect of the present disclosure relates to an endoscope system configured to be inserted into the body of a subject to examine or operate on tissues or the like and, more particularly, to an endoscope system in which the bending operation of a bendable section of an insertion tube is electromechanically actuated, thereby providing convenience to a doctor in operating the endoscope system.

BACKGROUND ART

The information disclosed in this section is only provided for an understanding of background information of embodiments of the present disclosure and should not be taken as a description of the prior art.

An endoscope generally refers to a medical instrument for examining the interior of the body for medical purposes. The endoscope may be referred to as "bronchoscope," "gastric endoscope," "laparoscope," or "colonoscope" depending on the area to be examined. Unlike most medical imaging devices, the endoscope is inserted directly into the body.

Due to the development of optical technology, the development of optical fibers, and the rapid development of electronics, endoscope technology has reached the stage of the current electronic endoscope and has made a great contribution to the development of the field of gastroenterology. With the development of the electronic endoscope, the electronic endoscope is used not only in the diagnostic field to directly look into and perform histological examination of a subject's body, but also may replace invasive surgery due to the rapid development of various treatment endoscopes.

The endoscope may generally include: a front part in which a biopsy channel, an illumination lens, an air/water nozzle, a camera, and the like are disposed; a bendable section bendable in the direction of a target; an insertion tube internally protecting an optical fiber from being twisted or deformed; and a control body capable of controlling suction, supply of air/water, and the like and in which a variety of switches for capturing and storing images are disposed.

The bending operation of the bendable section is controlled by respectively pulsing a plurality of wires. In this regard, a variety of mechanical components, such as a chain, for controlling the bending of the bendable section are located within the control body. Direction adjustment knobs for operating the mechanical components are also provided. Thus, a doctor may manually control the bending operation.

However, such a structure may have problems in that as a doctor operates the endoscope, intuitiveness is low, fatigue increases, and it is difficult to integrate artificial intelligence (AI) technology with the operation.

The information disclosed in the Background section is technical information that the inventors possessed for, or acquired during, derivation of embodiments of the present disclosure and should not be taken as known technology disclosed to the public before the filing of the embodiments of the present disclosure.

DISCLOSURE

Technical Problem

Accordingly, an aspect of the present disclosure has been proposed to solve the above-described problems occurring in the related art, and an objective of the present disclosure is to provide an endoscope system having an electromechanically actuated bending operation in order to provide convenience to a doctor in using the endoscope.

Another objective of the present disclosure is to provide an endoscope system in which the bending operation may be electromechanically actuated such that artificial intelligence (AT) technology may be incorporated in the endoscope system. Thus, when a doctor only performs an operation of inserting an insertion tube into the body, a bendable section may automatically perform the bending operation to position itself within a curved internal organ and travel to a target point. Furthermore, a process required for endoscopy may be automatically performed.

Another objective of the present disclosure is to provide an endoscope system that is hygienic and durable due to having a structure that is easy to clean or sterilize after the endoscope is used, and has improved durability.

The objectives of the present disclosure are not limited to the aforementioned descriptions, and other objectives not explicitly disclosed herein will be clearly understood by a person having ordinary knowledge in the art from the description provided hereinafter.

Technical Solution

In order to achieve the above objectives, according to one aspect of the present disclosure, provided is an endoscope system including: an insertion tube including a tube tip including an image capturing means and an illuminating means, a bending section to which the tube tip is connected, the bending section being configured to bend in a predetermined direction to allow a target portion of a subject to be observed, and a flexible portion to which the bending section is connected, the flexible portion being configured to move flexibly so as to be smoothly inserted into the body of the subject;

a universal cord connected to an air source, a water source, or a suction source to provide air, water, or suction force to the insertion tube;

a control body connecting the insertion tube and the universal cord, and including at least one of a control means for controlling the bending angle of the bendable section, an air valve for adjusting air, a water valve for controlling water, and a suction valve for controlling suction force; and an external device to which the universal cord is connected, and in which a power source for bending the bendable section is provided.

In some embodiments, the external device may be an image processing device receiving and processing image information collected by the image capturing means. Another embodiment of the external device may be a light source device providing a light source to the illuminating means.

In some embodiments, the endoscope system may include a mechanical string having one side connected to the bending section and the other side connected to the power source of the external device to transfer power generated by the power source to the bending section in order to bend the bending section.

In some embodiments, the external device may include a first connector connected to the power source, the universal cord may include a second connector connected to the mechanical string. When the universal cord is fitted to the external device, the first connector and the second connector may interact with each other to transfer power generated by the power source to the mechanical string.

In some embodiments, the endoscope system may include a compensator to perform a compensation function to prevent abnormal tension from affecting the maintenance of the attitude of the bendable section when the mechanical string has unexpected abnormal tension due to twisting, bending, or the like of the universal cord.

In some embodiments, the mechanical strings may include a first string disposed in the insertion tube and a second string coupled to the first string and disposed in the universal cord.

When unexpected abnormal tension is created due to twisting or bending of the universal cord, the first string and the second string may be decoupled within the control body to prevent abnormal tension from affecting to the maintenance of the attitude of the bendable section.

According to another aspect of the present disclosure, provided is an endoscope system including: an insertion tube configured to be inserted into a body of a subject to provide illumination and collect image information, and including a bending section configured to bend in a predetermined direction;

a control body connected to the insertion tube to control the bending of the bending section; and an external device configured to provide a light source for the illumination or process the image information, and including a power source to provide power to the bending section.

According to another aspect of the present disclosure, provided is an endoscope system including: an insertion tube including a tube tip including an image capturing means and an illuminating means, a bending section to which the tube tip is connected, the bending section being configured to bend in a predetermined direction to allow a target portion of a subject to be observed, and a flexible portion to which the bending section is connected, the flexible portion being configured to move flexibly so as to be smoothly inserted into the body of the subject;

a control body connected to a distal end of the insertion tube, including a control means for controlling a bending angle of the bending section, and dimensioned and configured to allow a user to easily hold the control body; and an external device connected to the control body and including a power source for bending the bending section.

Here, the external device may include an image processing device to receive and process image information collected by the image capturing means or a light source device to provide a light source to the illuminating means.

In some embodiments, the endoscope system may include a mechanical string having one side connected to the bending section and the other side connected to the power source of the external device to transfer power generated by the power source to the bending section in order to bend the bending section.

In this case, the external device may include a first connector connected to the power source, the control body may include a second connector connected to the mechanical string. When the universal cord is connected to the external device, the first connector and the second connector may interact with each other to transfer power generated by the power source to the mechanical string.

In some embodiments, the endoscope system may include a universal cord connecting the control body and the external device and configured to separate the control body from the external device, thereby allowing the user to easily move the control body while holding the control body.

In this case, the endoscope system may include a mechanical string having one side connected to the bending section and the other side connected to the power source of the external device to transfer power generated by the power source to the bending section in order to bend the bending section. The mechanical string may be disposed within the universal cord.

In this case, the external device may include a first connector connected to the power source, the universal cord may include a second connector connected to the mechanical string. When the universal cord is connected to the external device, the first connector and the second connector may interact with each other to transfer power generated by the power source to the mechanical string.

According to another aspect of the present disclosure, provided is an endoscope system including an endoscope module including an insertion tube and a control body. The insertion tube may include a tube tip including an image capturing means and an illuminating means, a bending section to which the tube tip is connected, the bending section being configured to bend in a predetermined direction to allow a target portion of a subject to be observed, and a flexible portion to which the bending section is connected, the flexible portion being configured to move flexibly so as to be smoothly inserted into the body of the subject.

The control body may be connected to the insertion tube, include a control means for controlling a bending angle of the bending section, and be dimensioned and configured to allow a user to easily hold the control body.

The endoscope system may include an external device connected to the control body and including a power source for bending the bending section.

According to another aspect of the present disclosure, provided is an endoscope system including: a light source device including a power source; and an endoscope module connected to the light source device to be provided with a light source and receive power generated by the power source, and including a bending section configured to bend using the power.

Advantageous Effects

According to an embodiment of the present disclosure, the endoscope system has an electromechanically actuated bending operation in order to provide convenience to a doctor in using the endoscope.

According to another embodiment of the present disclosure, the bending operation of the endoscope system may be electromechanically actuated such that artificial intelligence (AI) technology may be incorporated in the endoscope system. Thus, when a doctor only performs an operation of insetting an insertion tube into the body, a bendable section may automatically perform the bending operation to position itself within a curved internal organ and travel to a target point. Furthermore, a process required for endoscopy may be automatically performed.

According to another embodiment of the present disclosure, the endoscope system is hygienic due to having a structure that is easy to dean or sterilize after the endoscope is used, and has improved durability.

In addition, the present disclosure has a variety of effects with excellent versatility depending on the embodiment, and such effects may be clearly understood from the following description of embodiments.

DESCRIPTION OF DRAWINGS

The following drawings accompanying the specification illustrate embodiments of the present disclosure and, together with the foregoing disclosure, serve to provide further understanding of the technical spirit of the present disclosure, and thus, the present disclosure should not be construed as being limited to the drawings, wherein.

MODE FOR INVENTION

Advantages and features of the present disclosure, as well as methods of realizing the same, will be more clearly understood from the following detailed description of embodiments when taken in conjunction with the accompanying drawings. However, the present disclosure is not limited to specific embodiments to be described hereinafter but should be understood as including a variety of modifications, equivalents, and alternatives within the spirit and scope of the present disclosure. Rather, these embodiments are provided so that the description of the present disclosure will be complete and will fully convey the scope of the present disclosure to a person having ordinary skill in the art in the technical field to which the present disclosure pertains. In the following description of the present disclosure, a detailed description of related known technology will be omitted when the description may render the subject matter of the present disclosure unclear.

Figure 1:
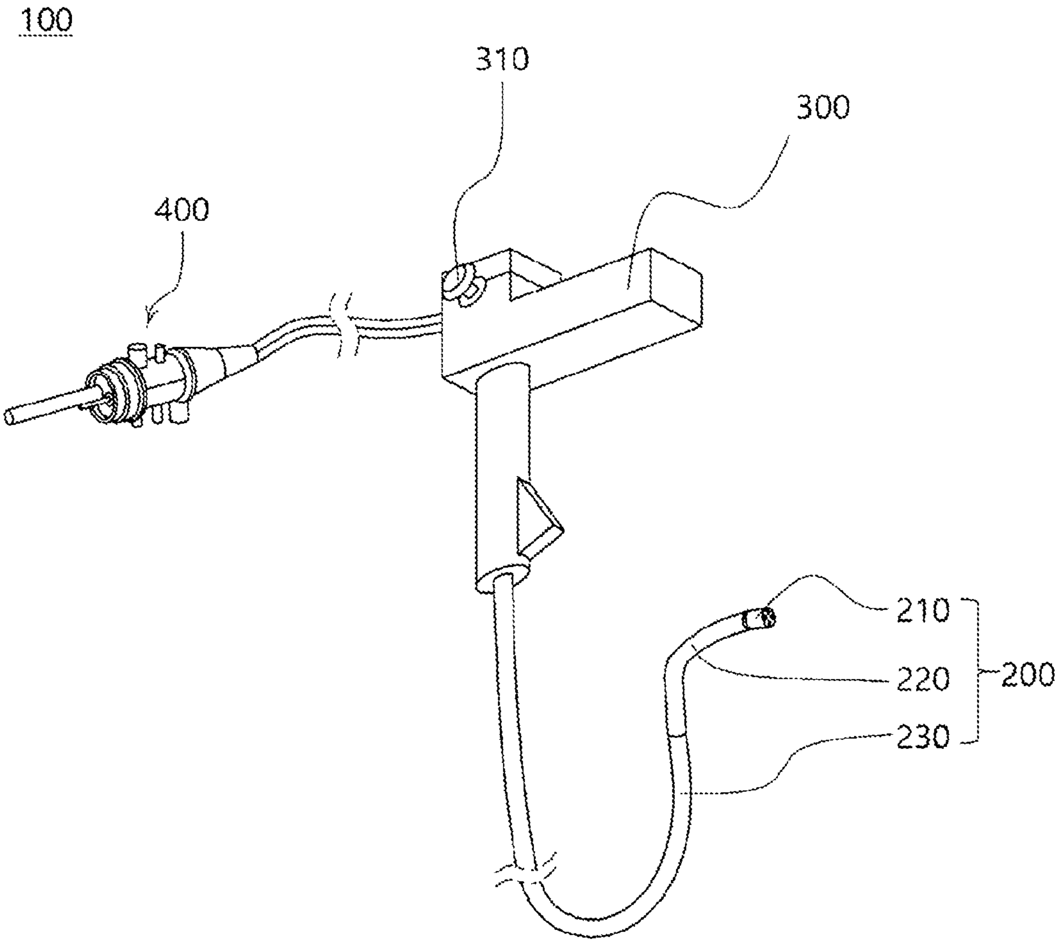
FIG. 1 illustrates an endoscope module of an endoscope system according to an embodiment of the present disclosure.

FIG. 1 illustrates an endoscope module of an endoscope system according to an embodiment of the present disclosure.

Figure 2:
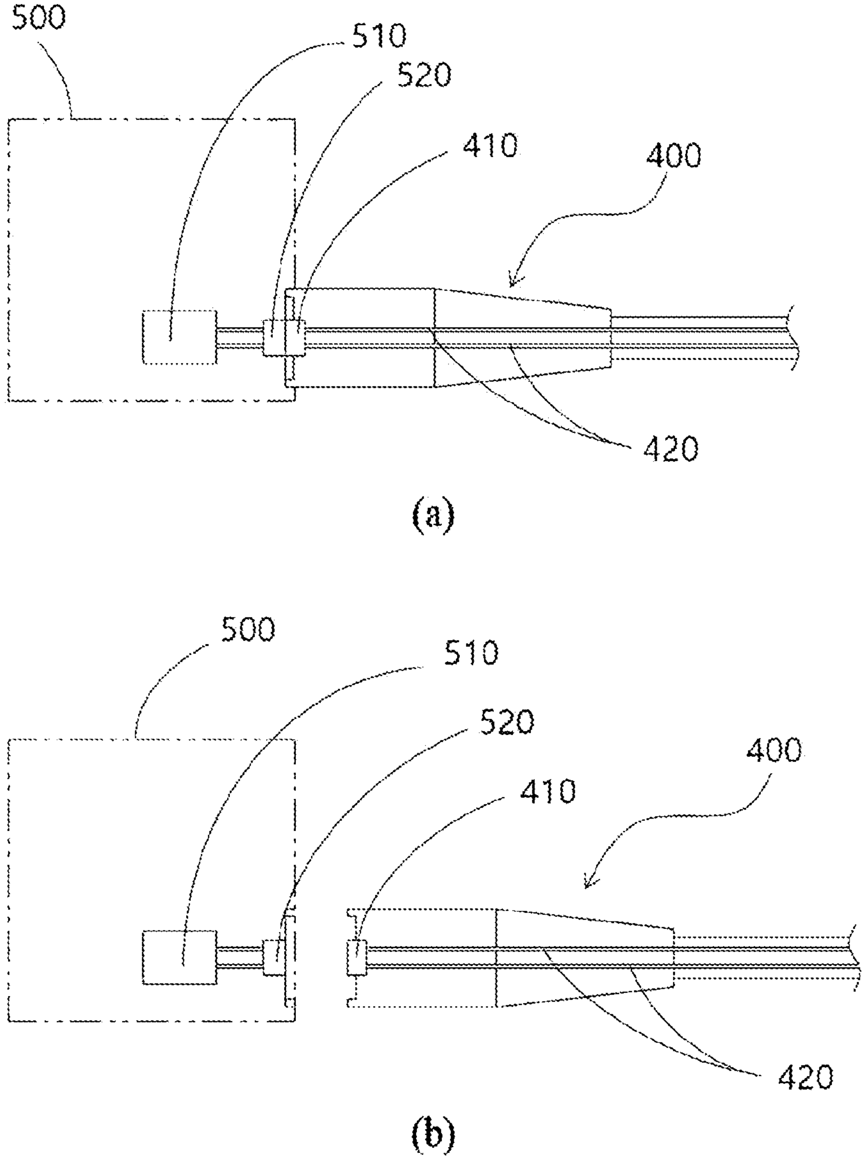
FIG. 2 illustrates a situation in which a first connector and a second connector are connected as the universal cord according to an embodiment of the present disclosure is fitted to an external device.

In addition, FIG. 2 illustrates a situation in which a first connector and a second connector are connected as the universal cord according to an embodiment of the present disclosure is fitted into an external device. FIG. 2(*a*) illustrates a situation in which the universal cord is fitted to the external device, and FIG. 2(*b*) illustrates a situation in which the universal cord is separated from the external device.

The endoscope system according to an embodiment of the present disclosure may include: an insertion tube 200 including a tube tip 210 having an image capturing means and an illuminating means, a bendable section 220 to which the tube tip 210 is connected, the bendable section 220 being configured to bend in a predetermined direction to allow a target portion of a subject to be observed, and a flexible portion 230 to which the bendable section 220 is connected, the flexible portion 230 being configured to move flexibly so as to be smoothly inserted into the body of the subject;

a universal cord 400 connected to an air source, a water source, or a suction source to provide air; water, or suction force to the insertion tube 200;

a control body 300 connecting the insertion tube 200 and the universal cord 400, and including at least one of a control means 310 for controlling the bending angle of the bendable section 220, an air valve for adjusting air, a water valve for controlling water, and a suction valve for controlling suction force; and an external device 500 to which the universal cord 400 is connected, and in which a power source 510 for bending the bendable section 220 is provided.

The insertion tube 200 is a component to be inserted into the body of the subject when a doctor performs an endoscopy. The insertion tube 200 may include the tube tip 210, the bendable section 220, and the flexible portion 230.

The tube tip 210 may be configured to be provided on a distal end of the bendable section 220 depending on the embodiment. The bendable section and the flexible portion 230 may be connected to form a single tube.

The tube tip 210 is located on the distal end of the bendable section 220 of the insertion tube 200 to be inserted into the body of the subject such that a variety of internal organs may be observed. The tube tip 210 may include at least one of an open portion through which a suction means and additional tools pass, an illuminating means for receiving light from a light source through an optical fiber and illuminating light to secure the field of view of a doctor, and an image capturing means for capturing images of internal organs and the like to collect and transfer image information.

The bendable section 220 may be provided in the shape of a mesh of woven metal wires. Mechanical strings (or wires) 420 may be accommodated within the mesh shape to realize the bending operation of the bendable section 220.

Since the bendable section 220 may be bent at a predetermined angle in all directions, i.e., back and forth and left and right, it is possible to examine the interior of the body of the subjective in all directions by combining this feature.

In addition, while the doctor is inserting the insertion tube 200 into the body of the subject in order to examine the interior of the body of the subject, the bendable section 220 may be bent at the predetermined angle to guide the movement of the tube tip 210 so that the tube tip 210 may smoothly move in the direction of a target to be examined.

The universal cord 400 may be connected to the air source, the water source, or the suction source to receive air, water, or suction force therefrom and transfer received air, water, or suction force to the tube tip 210. In this regard, a flow path allowing air or water to move therethrough may be formed within the universal cord 400. The flow path may also be formed within each of the control body and the insertion tube 200.

The doctor may operate the air valve, the water valve, or the suction valve provided in the control body 300 to eject air or water from the distal end of the insertion tube 200 or activate suction force on the distal end of the insertion tube 200.

The control body 300 may be provided with the control means 310 and function switches. The doctor may control the bending operation by means of the control means 310 of the control body 300 and select an air ejection function or a water ejection function or perform a suction function by means of the function switches. Here, the control means 310 includes, for example, a bending angle adjustment knob or a joystick.

The control means 310 may communicate with the power source 510 provided in the external device 500 through a wired or wireless medium. The doctor may transmit a control command to the power source 510 of the external device 500 by operating the control means 310. In response to the control command, the power source 510 may operate, thereby causing the bendable section 220 to perform the bending operation.

In some embodiments, the control means 310 may be a configuration including artificial intelligence (AI) technology and a communication module to receive a control command of the AI and transmit the control command to the power source 510. The AI may configure the target and the bending operation of the bendable section 220 to guide the movement toward the target and transmit the control command to perform the bending operation.

In the present specification, an assembly in which the insertion tube 200 and the control body 300 are coupled will be referred to as an 'endoscope module 100' depending on the embodiment.

In the present specification, an assembly in which the insertion tube 200, the control body 300, and the universal cord 400 are coupled will also be referred to as an 'endoscope module 100' depending on the embodiment.

That is, the endoscope module 100 may include the assembly of the insertion tube 200 and the control body 300 or the assembly of the insertion tube 200, the control body 300, and the universal cord 400, depending on the embodiment.

In addition, in the present specification, the 'external device 500' may refer to a device that is provided outside the endoscope module 100 and present as a separate article from the endoscope module 100. The doctor may use the endoscope module 100 after coupling the universal cord 400 to the external device 500. The universal cord 400 may be a configuration including a cord portion formed of a flexible material and a connecting portion configured to be directly connected to the external device 500.

The external device 500 may include an image processing device to receive and process image information collected by the image capturing means or a light source device to provide a light source to the illuminating means, depending on the embodiment. The external device 500 may include a device having both an image processing function and a light source function depending on the embodiment.

When the doctor performs histological examination using the endoscope, the endoscope module 100 may be inserted into the external device 500, for example, the light source device in order to illuminate the interior of the body to be observed by receiving a light source from the light source device. In addition, when the doctor fits the endoscope module 100 to the image processing device, image information of the interior of the body of the subject captured and collected using a camera may be transmitted to the image processing device. Then, the image may be processed, viewed, analyzed, and stored.

In addition, the external device 500 may be provided with the power source 510 for bending the bendable section 220. Here, the power source 510 may be a motor depending on the embodiment but is not limited thereto.

In some embodiments, the endoscope system may include the mechanical strings 420. Each of the mechanical strings 420 is configured such that one side is connected to the bendable section 220 and the other side is connected to the power source 510 of the external device 500. With this configuration, the mechanical strings 420 may transfer power generated by the power source 510 to the bendable section 220 in order to bend the bendable section 220.

In some embodiments, the external device 500 may include a first connector 520 connected to the power source 510, and the universal cord 400 of the endoscope module 100 may include a second connector 410 connected to the mechanical strings 420. When the universal cord 400 is disposed on the external device 500, the first connector 520 and the second connector 410 are coupled to each other and interact with each other to transfer power generated by the power source 510 to the mechanical strings 420.

In some embodiments, the first connector 520 may be disposed on a connecting portion of the external device 500 connected to the universal cord so as to be exposed to the outside. In addition, the second connector 410 may be disposed on a connecting portion of the universal cord 400 so as to be exposed to the outside. (Here, the connecting portion includes a portion directly connected to the external device 500). The second connector 410 may be disposed at a position corresponding to a position at which the first connector 520 of the external device 500 is disposed.

Due to this structure, when the user fits the connecting portion of the universal cord to the external device, the first connector 520 and the second connector 410 may be coupled.

Thus, when the user connects the endoscope module 100 to the external device 500, the exposed portion of the first connector 520 and the exposed portion of the second connector 410 may be electrically or mechanically coupled to interact. Consequently, power generated by the power source 510 of the external device 500 may be transferred to the mechanical strings 420. In addition, when the user separates the endoscope module 100 from the external device 500 to clean or sterilize the endoscope module 100, the first connector 520 and the second connector 410 are decoupled from each other.

A process in which the power source 510 provided in the external device 500 bends the bendable section 220 through the mechanical strings 420 according to the present embodiment will be described in detail. In the following description, the external device 500 is substituted by a light source device, and the power source 510 is substituted by a motor.

One end of each of the mechanical strings 420 may be connected to the bendable section 220 of the insertion tube 200, and the other end of each of the mechanical strings 420 may be connected to the second connector 410 disposed on the distal end of the universal cord 400. In this case, the mechanical strings 420 may be disposed to pass through the interiors of the universal cord 400, the control body 300, and the insertion tube 200.

In addition, the first connector 520 may be connected to the motor disposed within the light source device. In some embodiments, the motor may be additionally provided with a reducer to reduce and output motor power.

When the universal cord 400 of the endoscope module 100 is connected to the light source device, an optical fiber disposed within the endoscope module 100 to perform a light guide function may be connected to the light source and the illuminating means may be activated. A power supply disposed in the light source device and configured to supply various types of power is connected to the endoscope module 100 to supply power to the endoscope module 100. As the first connector 520 and the second connector 410 are coupled, the power of the motor may push or pull the mechanical strings 420, thereby causing the bendable section 220 to perform the bending operation.

The bendable section 220 may perform the bending operation back and forth and left and right. That is, a yawing operation and a pitching operation may be performed.

Although a pair of mechanical strings 420 are depicted in the drawings, a total of at least four mechanical strings 420 may be disposed. That is, a pair of mechanical strings 420 configured to perform the bending operation back and forth and a pair of mechanical strings 420 configured to perform the bending operation right and left may be disposed.

A plurality of motors may be provided. A motor for the forward and backward bending operation and a motor for the right and left bending operation may be provided separately.

The pair of mechanical strings 420 may operate in a one to one mapping manner, due to, for example, a configuration in which a chain and a gear are engaged or a configuration in which a pulley and a belt are engaged. For example, the mechanical strings 420 may operate so that when one mechanical string of the pair of mechanical strings 420 is pulled by 1, the other mechanical string of the pair of mechanical strings 420 is pushed.

In an embodiment of the present disclosure, the bendable section 220 is connected to the power source 510 of the external device 500 through the mechanical strings 420, and is controlled to bend due to power applied thereto through the mechanical strings 420. The structure in which the bendable section 220 is connected to and receives power from the power source 510 of the external device 500 is distinct from related-art technology in which the bendable section 220 is operated manually.

The insertion tube 200 of the related art has a structure in which the mechanical strings 420 capable of bending the bendable section 220 are provided, a mechanical device capable of pushing or pulling the mechanical strings 420 is disposed in the control body 300, and a bending angle adjustment knob allowing the control body 300 to be operated manually is provided on the control body 300. In addition, an air/water tube, a suction tube, electrical connecting lines, and the like are disposed and no power transmission configuration such as the mechanical strings 420 is disposed on the universal cord 400.

When the endoscope of the related art is used, the doctor may control the bending operation of the bendable section 220 by pulling the mechanical strings 420 by turning the knob while holding the control body 300 with one hand.

In this case, when the doctor inserts the insertion tube 200 through the oral cavity of the subject, for example, during gastroscopy, the tube tip 210 reaches a point at which the gullet and the respiratory tract are divided while moving through the interior of the body after passing through the oral cavity. At this point, even a skilled doctor takes a long time to control the bending operation of the bendable section 220 by manually operating the knob.

Due to the structure in which the bendable section 220 according to an embodiment of the present disclosure is connected to the power to receive power therefrom, manual operation of the doctor for controlling the bending operation may be minimized. Consequently, it may take a shorter time to reach the target point inside the body, and efforts may be reduced.

In addition, an unskilled doctor may get lost while moving toward the target in the darkness of the body. This problem may be solved, since the bending operation is electromechanically actuated and the endoscope may find the way by itself due to the AI applied thereto.

According to the present embodiment, when the direction of movement is detected using endoscope images and control values of the power source 510 are input on the basis of the direction of movement detected on the basis of the AI, the doctor is only required to smoothly insert the insertion tube 200 into the body. Then, the bending operation of the bendable section 220 is controlled by the AI, so that the insertion tube 200 may appropriately control the attitude thereof and accurately move through the interior of the body of the subject.

When the insertion tube 200 moves into the body of the subject, the AI may automatically detect a bend of a bent internal organ and the insertion tube may control the attitude thereof by itself. Thus, the doctor is not required to push buttons or move his/her body. That is, since the AI performs bending control in advance by independently determining whether an object is the gullet or the respiratory tract, the doctor is only required to push the insertion tube 200 through the oral cavity of the subject.

For example, in gastroscopy, in the case of pylorus or the like, the difference between the attitude of the tube 200 within the body and the attitude that the doctor is actually looking at is almost 180°. For the doctor to maintain this state while manually operating the endoscope system, a large amount of finger strength may be required. In particular, when the doctor is required to capture images in this state, more force may be required in the fingers, since substantial blurriness may be created even if the tube tip 210 shakes just a small amount. Thus, such an operation is significantly tiring for a doctor to perform.

However, there may be, for example, eight (8) targets, from which images must be captured during the examination on the pylorus. I this case, when the AI identifies these portions in advance and automatically captures images from these portions, the doctor is very convenient in a situation in which it is difficult to maintain the posture. According to the structure according to the present embodiment in which the bendable section 220 is connected to the power source 510 to receive power, the adjustment of the bending angle may be electromechanically actuated. The application of the AI may be enabled, thereby realizing a variety of functions. In the above-described situation, the convenience of use by the doctor may be obtained.

Since the endoscope system according to the present disclosure has a structure in which the power source 510 is disposed in the external device 500, the maintenance of the endoscope module 100 is easy.

Since the endoscope module 100 is configured to be inserted into the body of the subject, sanitation is very important. After the doctor has used the endoscope module for histological examination, it is essentially required to clean or sterilize the module.

To clean the endoscope module, it is required to use a detergent including a chemical diluted in water. However, a motor, i.e., a power source, is vulnerable to moisture, and thus, exposure of the motor to moisture is vital to the life span of the endoscope module.

Since the endoscope module is very expensive, when the endoscope module has a structure in which the power source 510 such as a motor is disposed within the control body 300, the user is required to be very careful so that water does not enter the endoscope module, and thus it is inconvenient to clean the endoscope module. When the user is concerned that moisture would enter the motor and cause the motor to fail and thus may not properly clean the endoscope module, a fatal problem for sanitation may occur. Since the endoscope module is expensive, when the entire article must be replaced due to the failure of an internal component such as the motor, it is very uneconomical for the user.

The endoscope system according to an embodiment of the present disclosure may fundamentally remove the above-described problems, since the motor is mounted on the external device 500 provided as a separate article from the endoscope module 100. That is, after the endoscope module is used, the doctor cleans the endoscope module by separating the endoscope module from the external device 500. Since the endoscope module is not provided with the power source 510 such as a motor, there is no concern that water may enter the motor, and thus, it is possible to comfortably clean the endoscope module.

Figure 3:
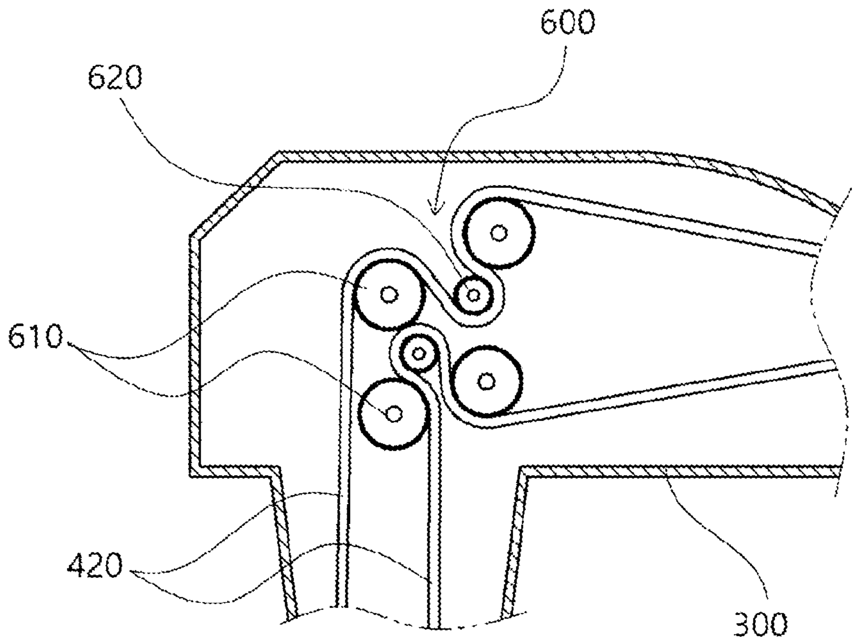
FIG. 3 illustrates an example of a compensator disposed on the control body according to an embodiment of the present disclosure.

FIG. 3 illustrates an example of a compensator disposed on the control body according to an embodiment of the present disclosure.

The endoscope system according to an embodiment of the present disclosure may include a compensator 600 adjusting the movement of the mechanical strings 420.

Here, the compensator 600 may perform a compensation function to adjustment the movement of the mechanical strings 420 in order to prevent the bending angle of the bendable section 220 from changing due to an unexpected external input.

For example, when the mechanical strings 420 have unexpected abnormal tension due to twisting, bending, or the like of the universal cords 400, the compensator 600 may perform a compensation function to prevent abnormal tension from affecting the maintenance of the attitude of the bendable section 220 (where the maintenance of attitude includes the maintenance of the bending angle).

In some embodiments, the compensator 600 may be disposed within the control body 300 or the universal cord 400. In some embodiments, the compensator 600 may be disposed within the external device 500.

Referring to FIG. 3, according to an embodiment of the compensator 600, an idler pulley 620 is used. In this case, according to an embodiment of the compensator 600, within the control body 300, one of the pair of mechanical strings 420 is connected to a pair of main pulleys 610 and the idler pulley 620, and the other of the pair of mechanical strings 420 is connected to the pair of main pulleys 610 and the idler pulley 620 in the same manner. The mechanical strings 420 are provided as two sets of mechanical strings comprised of a pair of mechanical strings for bending in the back and forth direction and a pair of mechanical strings for bending in the transverse direction, and thus the compensator 600 is also required to have a configuration matching the mechanical strings 420.

During an operation, when an operator steps on the universal cord 400 and abnormal tension is created, the idler pulley 620 moves to remove the tension. Thus, there is no change in the tension of the mechanical strings 420 in the insertion tube 200. In this manner, the attitude of the bendable section 220 may be maintained.

Figure 4:
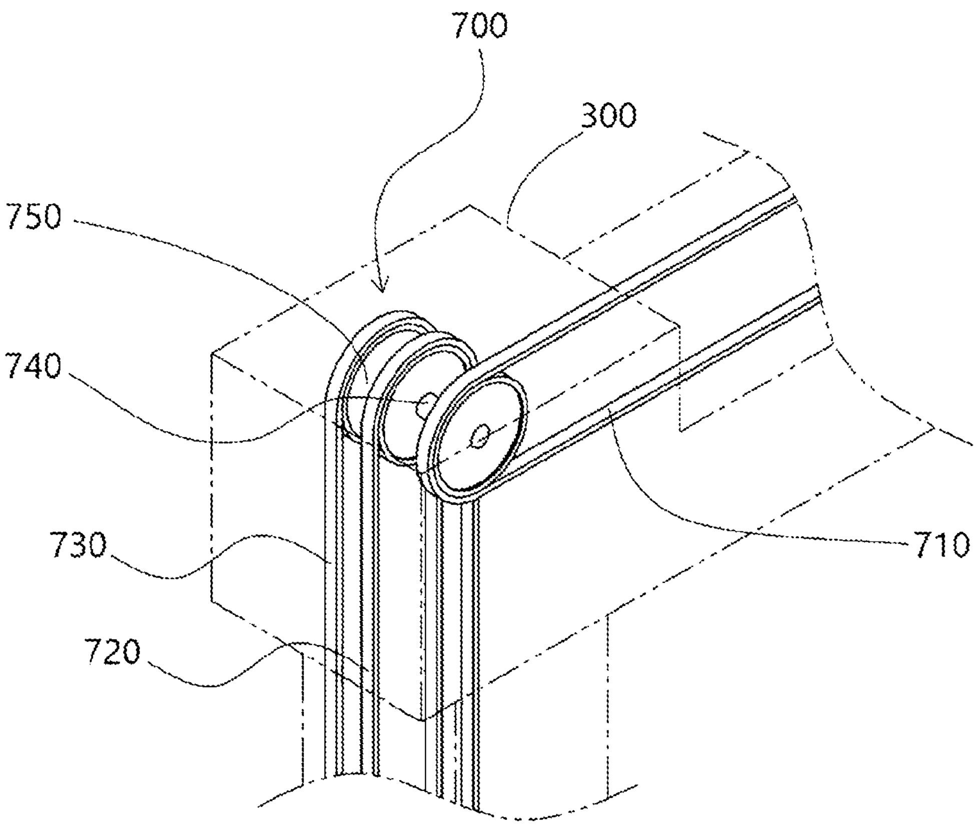
FIG. 4 illustrates an example of a compensator disposed on a control body according to another embodiment of the present disclosure.

FIG. 4 illustrates an example of a compensator disposed on a control body according to another embodiment of the present disclosure.

According to another embodiment in which compensation may be performed, the mechanical strings 420 include a first string 710 disposed in the insertion tube 200 and a second string 720 coupled to the first string 710 and disposed in the universal cord 400.

When unexpected abnormal tension is created due to twisting or bending of the universal cord 400, the first string 710 and the second string 720 may be decoupled within the control body to prevent abnormal tension from affecting to the maintenance of the attitude of the bendable section.

According to the structure of the compensator 600 according to the present embodiment, a connecting pulley assembly 700 comprised of a plurality of pulleys 750 connected through a compensation shaft 740 capable of relatively rotating is disposed on the control body 300, the first string 710 withdrawn toward the insertion tube 200 and connected to the bendable section 220 and the second string 720 withdrawn toward the universal cord 400 and connected to the second connector 410 are coupled to the pulleys 750, respectively, and tension sensors for detecting tension of the first string 710 and the second string 720, respectively, are disposed.

At ordinary times, when the second string 720 of the universal cord 400 is driven by the power source 510 disposed in the extern& device 500, the first string 710 coupled to the second string 720 in a one to one relationship is driven using the connecting pulley assembly 700, thereby adjusting the bending angle.

However, when abnormal tension in the second string 720 is detected due to the twisting or the bending of the universal cord 400, two pulleys of the connecting pulley assembly 700 are directly decoupled, and no abnormal tension is created in the first string 710. As a result, the bendable section 220 may maintain the bending angle.

In some embodiments, whether or not abnormal tension is created may be determined by comparing sensing values of a pair of tension sensors detecting the tension of the first string and the tension of the second string 720.

When abnormal tension is detected, the first string 710 remains coupled to the second string 720 before decoupling for compensating for abnormal tension is performed. Thus, when the first string 710 is twisted, the second string 720 is also affected by abnormal tension so as to be twisted. Thus, the attitude of the bendable section 220 is also affected. In this case, a compensation operation for recovering the first string 710 is required so that the bendable section 220 may maintain a correct attitude. For this recovery, a third string 730 separately connected to the power source 510 may be coupled to the pulley 750 to which the first string 710. When abnormal tension is detected, the compensation operation of the third string 730 may also be enabled together with the decoupling, thereby recovering the first string 710 and the bendable section 220 to the original correct attitude.

For example, since the tension sensors are disposed on the universal cord 400 side and the insertion tube 200 side, respectively, when the second string 720 has abnormal tension as the universal cord 400 is twisted or bent, corresponding opposing force may be provided. In a case in which force 0 is supposed to be input to the tension sensor on the universal cord 400 side due to twisting of the universal cord 400, when force 0 is input, it is required to input force −1 to the tension sensor on the insertion tube 200 side so that the attitude of the bendable section 220 may be maintained.

Thus, control may be performed to apply force −1 to the tension sensor on the insertion tube 200 side by adjusting the third string 730.

In addition, another compensation embodiment includes a controller capable of collecting sensing values from the tension sensors and, when abnormal tension is detected, directly sending a control command to the power source 510, such as the motor, so that the motor may directly provide power for recovery. The controller may be disposed on the control body 300 or the external device 500 depending on the embodiment.

When the endoscope module is used, the doctor operates the switch or the control means 310 by holding the control body 300 with one hand. In this case, even if the insertion tube 200 is inserted in the body of the subject and is performing tasks, for example, by moving in search for targets, the universal cord 400 is exposed to the outside and remains unattended. Thus, the universal cord 400 may be stepped on or be bent or twisted by unexpected external force.

Unlike the related art, in the endoscope module according to an embodiment of the present disclosure, the mechanical strings 420 are disposed in the universal cord 400, and thus the mechanical strings 420 may have abnormal tension due to twisting, bending, or the like of the universal cord 400. In the related art, such a problem does not occur, since the universal cord 400 is not provided with the mechanical strings 420.

When the mechanical strings 420 have abnormal tension, the maintenance of the attitude of the bendable section 220 performing a task inside the body of the subject is affected. For example, in a case in which the bendable section 220 is required to maintain a specific attitude to capture images from specific targets, the task may not be performed when the maintenance of the attitude fails due to abnormal tension.

When the compensator 600 according to an embodiment of the present disclosure is applied, the above-described problems may be overcome, and abnormal tension caused by unexpected situations, external force, and the like may be overcome.

In addition, another aspect of the present disclosure may provide an endoscope system including: an insertion tube 200 including a tube tip having an image capturing means and an illuminating means, a bendable section 220 to which the tube tip is connected, the bendable section 220 being configured to bend in a predetermined direction to allow a target portion of a subject to be observed, and a flexible portion to which the bendable section 220 is connected, the flexible portion being configured to move flexibly so as to be smoothly insetted into the body of the subject;

- a control body 300 connected to a distal end of the insertion tube 200, including a control means 310 for controlling the bending angle of the bendable section 220, and dimensioned and configured to allow a user to easily hold the control body 300; and
- an external device 500 connected to the control body 300 and including a power source 510 for bending the bendable section 220.

Here, the user may include a doctor using the endoscope system.

Here, the external device 500 may include an image processing device to receive and process image information collected by the image capturing means or a light source device to provide a light source to the illuminating means, depending on the embodiment.

The endoscope system may include mechanical strings 420 depending on the embodiment. Each of the mechanical strings 420 is configured such that one side is connected to the bendable section 220 and the other side is connected to the power source 510 of the external device 500. With this configuration, the mechanical strings 420 may transfer power generated by the power source 510 to the bendable section 220 in order to bend the bendable section 220.

That is, the mechanical strings 420 may be configured to extend through the insertion tube 200 and the control body 300 to be connected to the power source 510 provided in the external device 500. Thus, power generated by the power source 510 provided within the external device 500 may be transferred to the bendable section 220.

In this case, the external device 500 includes the first connector 520 connected to the power source 510, and the control body 300 includes the second connector 410 connected to the mechanical strings 420. When the control body 300 is connected to the external device 500, the first connector 520 and the second connector 410 may interact with each other to transfer power generated by the power source 510 to the mechanical strings 420.

When the control body 300 and the external device 500 are disconnected, the first connector 520 and the second connector 410 stop interacting, and the user may clean an assembly of the control body 300 and the insertion tube 200 with water. Even when cleaned with water, there is no risk that the power source 510 may fail due to contact with cleaning water, since the power source 510 is disposed in the external device 500 instead of in the control body 300 or the insertion tube 200.

In addition, according to another embodiment, the endoscope system may include a universal cord 400 connecting the control body and the external device 500. The universal cord 400 may separate the control body from the external device 500 so that the user may easily move the control body while holding the control body.

In this case, the endoscope system may include the mechanical strings 420. Each of the mechanical strings 420 is configured such that one side is connected to the bendable section 220 and the other side is connected to the power source 510 of the external device 500. With this configuration, the mechanical strings 420 may transfer power generated by the power source 510 to the bendable section 220 in order to bend the bendable section 220. The mechanical strings 420 may be disposed within the universal cord 400.

That is, the mechanical strings 420 may be disposed to extend through the universal cord 400, the control body 300, and the insertion tube 200.

Here, the external device 500 includes the first connector 520 connected to the power source 510, and the universal cord 400 includes the second connector 410 connected to the mechanical strings 420. When the universal cord 400 is connected to the external device 500, the first connector 520 and the second connector 410 may interact with each other to transfer power generated by the power source 510 to the mechanical strings 420. When the universal cord 400 is disconnected from the external device 500, the first connector 520 and the second connector 410 stop interacting.

In this case, the power source 510 is disposed in the external device 500, but is not disposed in the endoscope module, i.e., an assembly of the universal cord 400, the control body 300, and the insertion tube 200. Thus, even when the user cleans the endoscope module with a cleaning agent such as water, there is no risk that the power source 510 may be wet with water to fail.

In some embodiments, a compensator 600 may be provided. When unexpected abnormal tension is created within the control body 300 due to twisting, bending, or the like of the universal cord 400, the compensator 600 performs a compensation function so as to prevent abnormal tension from affecting the maintenance of the attitude of the bendable section 220. The compensator 600 may be substantially the same as the compensator 600 described in the foregoing embodiment, and thus a detailed description thereof will be omitted.

In some embodiments, the mechanical strings 420 may include a first string 710 disposed in the insertion tube 200 and a second string 720 coupled to the first string 710 and disposed in the universal cord 400.

When unexpected abnormal tension is created due to twisting or bending of the universal cord 400, the mechanical strings 420 may be decoupled within the control body 300 to prevent abnormal tension from affecting to the maintenance of the attitude of the bendable section 220. That is, the mechanical strings 420 may be separated. This structure may be the same as the decoupling structure including the pulleys 750, the compensation shaft 740, and the third string 730 described in the foregoing embodiment, and thus a detailed description thereof will be omitted.

Another embodiment of the present disclosure may provide an endoscope system including: a light source device including a power source 510; and a bendable section 220 connected to the light source device to be provided with a light source and configured to receive power generated by the power source 510 and be bent by the received power.

Here, the light source device may include a device including a light source such as an LED, i.e., a device providing the light source to the endoscope module. For example, the light source device may refer to the external device 500 mentioned in the foregoing embodiment, i.e., the light source device or the image processing device.

Here, the power source 510 may include a motor configuration mentioned in the foregoing embodiment.

Here, the bendable section 220 may refer to a configuration having substantially the same function as the bendable section 220 included in the endoscope module 100 mentioned in the foregoing embodiment.

Here, the endoscope module 100 may include a compensator configuration performing a compensation function to prevent the bending angle of the bendable section 220 from changing arbitrarily due to an unexpected external input.

The compensator configuration has been described above in the foregoing embodiment, and thus a detailed description thereof will be omitted.

In the specification of the present disclosure, the use of the term "above" and similar denoting terms may correspond to both singular and plural forms. Furthermore, recitation of ranges of values herein are merely intended to refer to respective separate values falling within the respective ranges and, unless otherwise indicated herein, the respective separate values are incorporated herein as if individually recited herein.

Finally, the operations of any method described herein may be performed in any suitable order unless otherwise indicated herein or otherwise clearly contradicted by the context. However, the operations shall not be limited to the described sequence. The use of any examples or exemplary languages (e.g., "such as") provided herein, is intended merely to better illustrate the present disclosure and does not pose a limitation on the scope of the present disclosure unless otherwise defined by the Claims. In addition, a person having ordinary knowledge in the art will appreciate that various modifications, combinations, and changes are possible according to design conditions and factors within the scope of the Claims or equivalents thereof.

Therefore, the spirit of the present disclosure shall not be limited to the above-described embodiments, and the entire scope of the appended claims and equivalents thereof will fall within the scope and spirit of the present disclosure.

DESCRIPTION OF REFERENCE NUMERALS OF DRAWINGS

100: endoscope system
200: insertion tube
210: tube tip
220: bendable section
230: flexible portion
300: control body
310: control means
400: universal cord
410: second connector
420: mechanical string
500: external device
510: power source
520: first connector
600: compensator
610: main pulley
620: idler pulley
700: connecting pulley assembly
710: first string
720: second string
730: third string
740: compensation shaft
750: pulley

The invention claimed is:

1. An endoscope system comprising:

an insertion tube comprising a tube tip including an image capturing means and an illuminating means, a bending section to which the tube tip is connected, the bending section being configured to bend in a predetermined direction to allow a target portion of a subject to be observed, and a flexible portion to which the bending section is connected, the flexible portion being configured to move flexibly so as to be smoothly insetted into the body of the subject;

a control body connected to the insertion tube, comprising a control means for controlling a bending angle of the bending section, and dimensioned and configured to allow a user to easily hold the control body;

an external device connected to the control body and comprising a power source for bending the bending section;

a universal cord connecting the control body and the external device;

a mechanical string transferring power generated by the power source to the bending section in order to bend the bending section, wherein the mechanical string is disposed to pass through the interiors of the universal cord, the control body, and the insertion tube; and a compensator to perform a compensation function to prevent abnormal tension from affecting the maintenance of the attitude of the bending section when the mechanical string has unexpected abnormal tension, wherein the compensator comprises a connecting pulley assembly including a plurality of pulleys connected through a compensation shaft capable of relatively rotating and the connecting pulley assembly is disposed on the control body, wherein the mechanical string comprises a first string disposed in the insertion tube and a second string coupled to the first string via the connecting pulley assembly and disposed in the universal cord, wherein the first string is coupled to one of the plurality of pulleys, and the second string is coupled to another of the plurality of pulleys, wherein when unexpected abnormal tension is generated in the second string, two pulleys of the connecting pulley assembly are decoupled, and abnormal tension is not transmitted to the first string.

2. The endoscope system according to claim 1, wherein the external device comprises an image processing device to receive and process image information collected by the image capturing means or a light source device to provide a light source to the illuminating means.

3. The endoscope system according to claim 1, wherein the external device includes a first connector connected to the power source, the universal cord includes a second connector connected to the mechanical string, and when the universal cord is connected to the external device, the first connector and the second connector interact with each other to transfer power generated by the power source to the mechanical string.

4. An endoscope system comprising:

an insertion tube configured to be inserted into a body of a subject to provide illumination and collect image information, and comprising a bending section configured to bend in a predetermined direction;

a control body connected to the insertion tube to control the bending of the bending section;

an external device configured to provide a light source for the illumination or process the image information, and comprising a power source to provide power to the bending section;

a universal cord connecting the control body and the external device;

a mechanical string transferring power generated by the power source to the bending section in order to bend the bending section, wherein the mechanical string is disposed to pass through the interiors of the universal cord, the control body, and the insertion tube; and a compensator to perform a compensation function to prevent abnormal tension from affecting the maintenance of the attitude of the bending section when the mechanical string has unexpected abnormal tension, wherein the compensator comprises a connecting pulley assembly including a plurality of pulleys connected through a compensation shaft capable of relatively rotating and the connecting pulley assembly is disposed on the control body, wherein the mechanical string comprises a first string disposed in the insertion tube and a second string coupled to the first string via the connecting pulley assembly and disposed in the universal cord, wherein the first string is coupled to one of the plurality of pulleys, and the second string is coupled to another of the plurality of pulleys, wherein when unexpected abnormal tension is generated in the second string, two pulleys of the connecting pulley assembly are decoupled, and abnormal tension is not transmitted to the first string.

* * * * *